(12) United States Patent
Dunlap

(10) Patent No.: US 7,730,888 B2
(45) Date of Patent: Jun. 8, 2010

(54) NASOPHARYNGEAL AIRWAY DEVICE AND METHOD OF USE

(75) Inventor: Ivan L. Dunlap, St. George, UT (US)

(73) Assignee: Spivan, LLC, Las Vegas, NV (US)

( * ) Notice: Subject to any disclaimer, the term of this patent is extended or adjusted under 35 U.S.C. 154(b) by 922 days.

(21) Appl. No.: 11/468,158

(22) Filed: Aug. 29, 2006

(65) Prior Publication Data
US 2006/0283464 A1  Dec. 21, 2006

Related U.S. Application Data

(63) Continuation-in-part of application No. 10/936,940, filed on Sep. 9, 2004, now Pat. No. 7,100,612.

(51) Int. Cl.
*A61M 15/08* (2006.01)
(52) U.S. Cl. .................................. 128/207.18
(58) Field of Classification Search ............ 128/207.18; 604/174, 523, 540
See application file for complete search history.

(56) References Cited

U.S. PATENT DOCUMENTS

| | | | |
|---|---|---|---|
| 2,335,936 A | * | 12/1943 | Hanlon ........................ 606/199 |
| 2,822,809 A | | 2/1958 | Sollmann |
| 3,161,199 A | * | 12/1964 | Sands ......................... 604/179 |
| 3,568,678 A | | 3/1971 | Pourquier |
| 4,402,684 A | | 9/1983 | Jessup |
| 4,736,741 A | * | 4/1988 | Payton et al. ........... 128/207.18 |
| 5,556,385 A | * | 9/1996 | Andersen .................... 604/174 |
| 5,664,567 A | | 9/1997 | Linder |
| 5,937,858 A | | 8/1999 | Connell |
| 6,328,753 B1 | | 12/2001 | Zammit |
| 6,789,538 B2 | | 9/2004 | Wright et al. |
| 2003/0136413 A1 | | 7/2003 | Brain et al. |

* cited by examiner

*Primary Examiner*—Justine R Yu
*Assistant Examiner*—Christopher Blizzard
(74) *Attorney, Agent, or Firm*—Workman Nydegger

(57) ABSTRACT

A method includes advancing a distal end of a tubular nasopharyngeal airway device through a nostril opening and into a nasal passageway of a patient, the nasopharyngeal airway device having a proximal end that is larger than the nostril opening. At least a terminal tip of a resiliently flexible elongated locking protrusion that projects from the proximal end of the nasopharyngeal airway device is inserted into the same nostril opening in which the nasopharyngeal airway device is disposed so that the locking protrusion biases against the lining of the nasal passageway, thereby securing the nasopharyngeal airway device within the nasal passageway.

15 Claims, 7 Drawing Sheets

NASOPHARYNGEAL AIRWAY DEVICE AND METHOD OF USE

CROSS-REFERENCE TO RELATED APPLICATIONS

This application is a continuation-in-part of U.S. patent application Ser. No. 10/936,940, filed Sep. 9, 2004, now U.S. Pat. No. 7,100,612, issued Sep. 5, 2006, which application is incorporated herein by reference in its entirety.

BACKGROUND OF THE INVENTION

1. The Field of the Invention

The present invention relates to nasopharyngeal airway devices and their methods of use.

2. The Relevant Technology

The medical industry uses nasopharyngeal airway devices to assist a patient in breathing. A typical nasopharyngeal airway device comprises an elongated tube having an opening located at the top end and at the bottom end so that air can pass therethrough. The devices is inserted into one of the nasal passageways of the patient, thereby providing an unobstructed passageway through which the patient can easily breath. For example, nasopharyngeal airway devices are commonly used in patients who are still under anesthesia following an operation and who may have some difficultly breathing. Once the patient is fully awake, the device can be removed.

An enlarged circular flange is located at the first end of the nasopharyngeal airway device so as to prevent the device from being slid too far into the nasal passageway of the patient. Natural movements of the patient, however, often cause the device to progressively slide out of the nasal cavity. As such, the medical staff must be continually vigilant to ensure that the nasopharyngeal airway device is continually retained within the nasal passageway so as to ensure proper breathing. This unwanted movement of the nasopharyngeal airway device not only creates risk to the patient's breathing but the continued reinsertion of the device can further irritate the lining of the nasal passageway.

It is appreciated that there are other additional shortcomings associated with conventional nasopharyngeal airway devices. For example, as a person breathes through their nose, humidity in the surrounding air provides moisture to the lining of the nasal passageway. By inserting the nasopharyngeal airway device into the nasal passageway, the air is no longer passing over the lining of the nasal passageway but is rather passing through the device. As a result, the nasopharyngeal airway device can result in drying out of the nasal passageway which in turn can cause irritation of the lining and/or nose bleeds.

Furthermore, sinus and other bodily fluids are continually delivered to the nasal passageway. These fluids typically flow back and down the throat of the patent. However, because conventional nasopharyngeal airway devices only have a single opening at the second end thereof, there is the potential risk that the single opening can become constricted or occluded by the fluids, thereby limiting that ability of the patient to breath through nasopharyngeal airway devices.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

The present invention is directed to nasopharyngeal airway devices that are selectively inserted within a nasal passageway of a patient and can be used for various purposes. For example, the devices are commonly used on patients coming out of anesthesia after an operation to provide them with an open airway through which they can easily breathe. The inventive nasopharyngeal airway devices can also be used to assist individuals with breathing who experience sleep apnea. Other potential uses for the device include, but are not limited to, administering anesthesia, administering nutrients or feedings, resuscitation, and the like.

Figure 1:
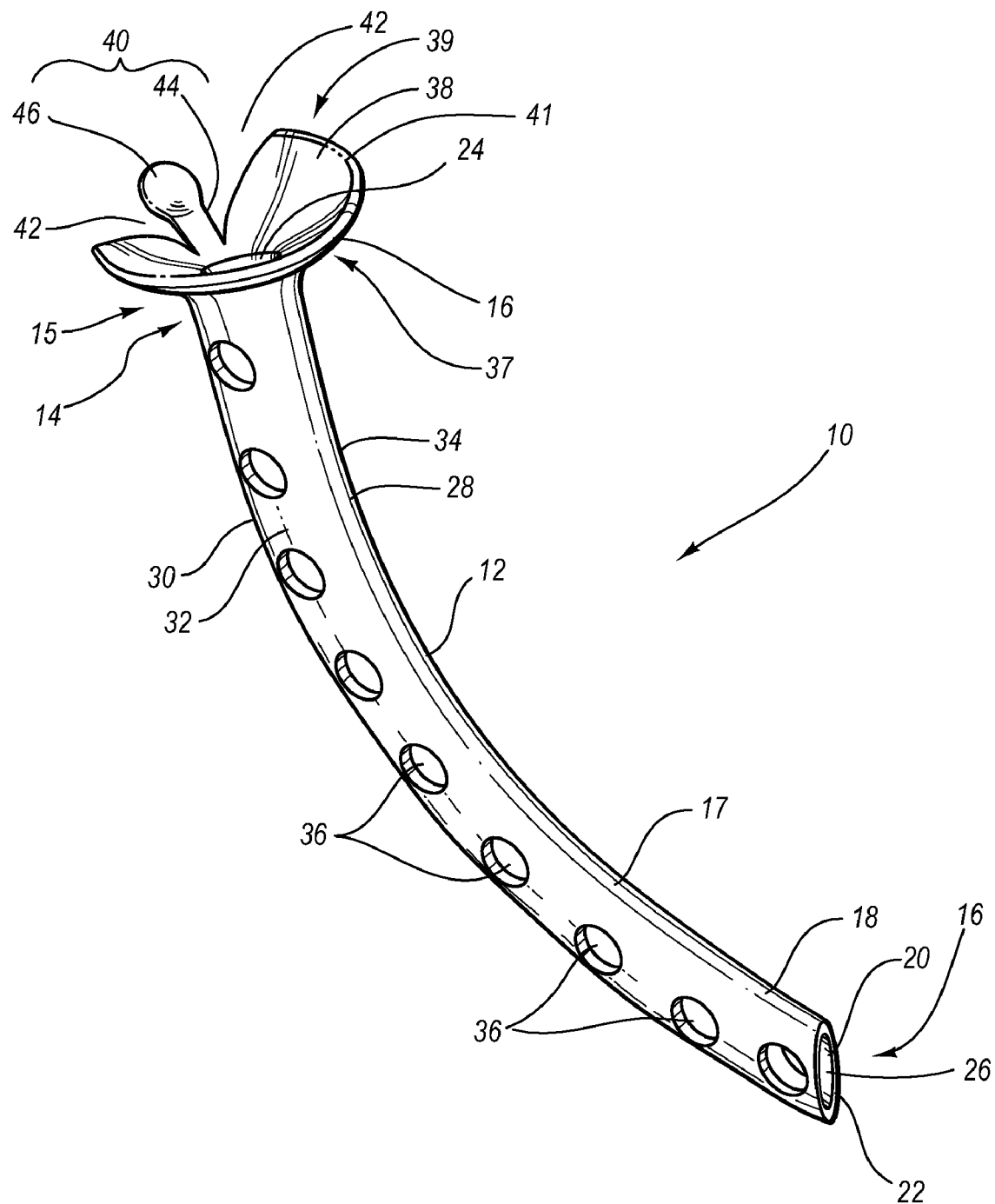
FIG. 1 is a perspective view of one embodiment of a nasopharyngeal airway device.

Depicted in FIG. 1 is one embodiment of a nasopharyngeal airway device 10 incorporating features of the present invention. Device 10 includes an elongated tubular body 12 in the form of a tube having a proximal end 14 and an opposing distal end 16. Tubular body 12 includes a sidewall 17 having an exterior surface 18 and an interior surface 20 extending between proximal end 14 and distal end 16. In one embodiment distal end 16 is tapered to facilitate easy insertion. Interior surface 20 bounds an air passage 22. Air passage 22 extends between proximal end 14 and distal end 16 of tubular body 12. Air passage 22 communicates with an opening 24 formed at proximal end 14 of tubular body 12 and an opening 26 formed at distal end 16 of tubular body 12. Air passage 22 is configured to allow air to freely pass between proximal end 14 and distal end 16 of tubular body 12. It is also envisioned that air passage 22 can be configured to receive feeding tubes or other tubes to deliver medications, other gases or the like.

Tubular body 12 is comprised of a soft, flexible material so as to minimize any irritation or trauma during insertion and use. The material should also be sterilizable. Suitable materials include rubber, biocompatible plastics such as silicone, organic plastic, and other polymeric materials. For example, soft polyvinyl chloride may be used.

Tubular body 12 is depicted with exterior surface 18 and interior surface 20 each having a substantially circular transverse cross section. In alternative embodiments, however, exterior surface 18 and/or interior surface 20 can have a transverse cross section that is elliptical, polygonal, irregular, or any other desired shape.

Furthermore, in the embodiment depicted in FIG. 1, tubular body 12 is curved along the length thereof This curvature generally complements the natural curvature of the nasal passageway and provides for easy insertion and retention of tubular body 12 within the nasal passageway. In alternative embodiments, it is appreciated that because tubular body 12 is flexible, it can also be linear or have other configurations.

Nasopharyngeal airway device 10 and tubular body 12 thereof can be formed having a variety of different sizes and configurations to accommodate different uses and different sizes of people. By way of illustration and not by limitation, in one embodiment air passage 22 can have a diameter in a range between about 5 mm to about 15 mm. The thickness of sidewall 17 of tubular body 12 is typically in a range from about 1 mm to about 3 mm. The length from proximal end 14 of tubular body 12 to distal end 16 of tubular body 12 is typically from about 10 cm to about 20 cm. Again, however, it is appreciated that other dimensions of tubular body 12 may be used depending on the intended purpose for which device 10 is used.

Figure 3:
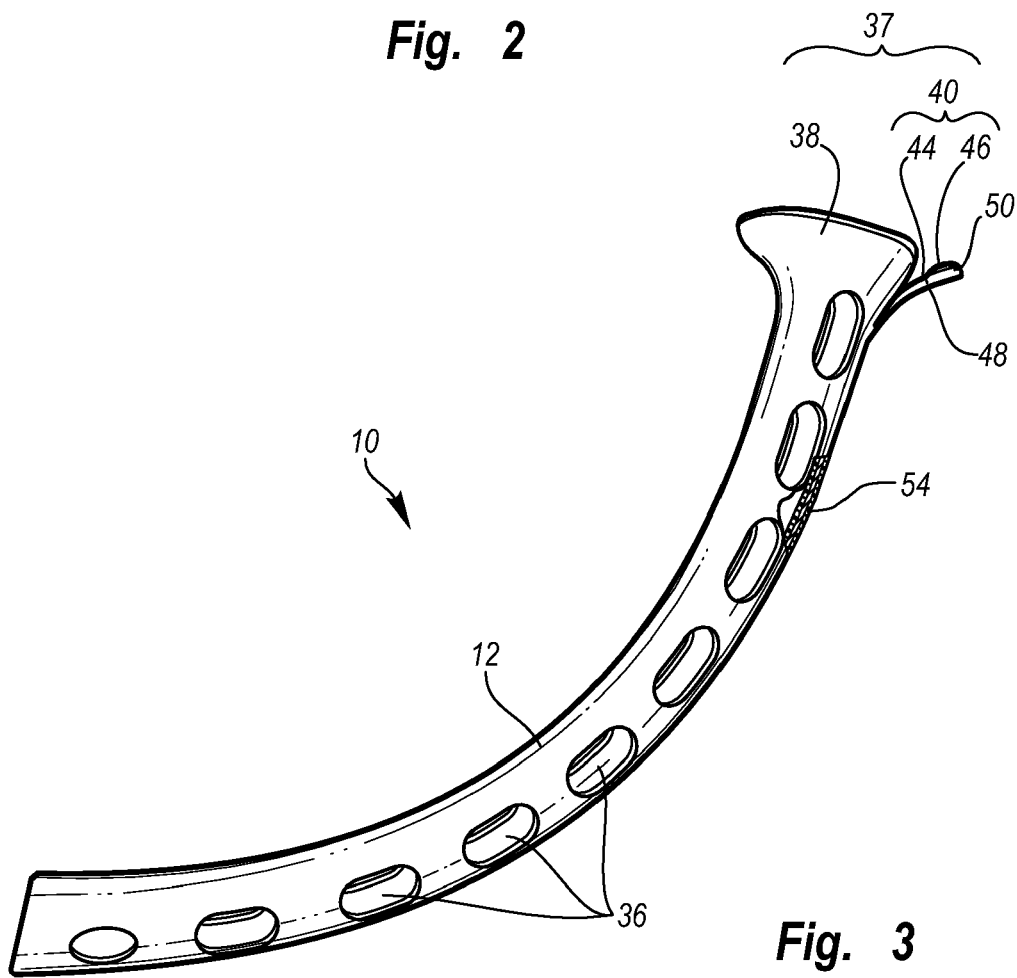
FIG. 3 a side view of the embodiment of FIG. 1.

Tubular body 12 can also be referenced as having a relative front side 28, a back side 30, a left side 32, and a right side 34. Front side 28 and back side 30 are disposed within the plane of curvature. Although not required, in one embodiment sides 32, 34 of tubular body 12 included a plurality of apertures 36 formed along the sidewall 17 of tubular body 12 so as to communicate with air passage 22. Apertures 36 can be formed at regular or irregular intervals along sidewall 17 of tubular body 12. It is also appreciated that apertures 36 can be formed on various regions of front side 28, back side 30 or can extend between various faces. It is also appreciated that apertures 36 can be any desired size, shape or configuration. For example, in contrast to being circular as shown in FIG. 1, the apertures 36 can be elongated as shown in FIG. 3.

Figure 6:
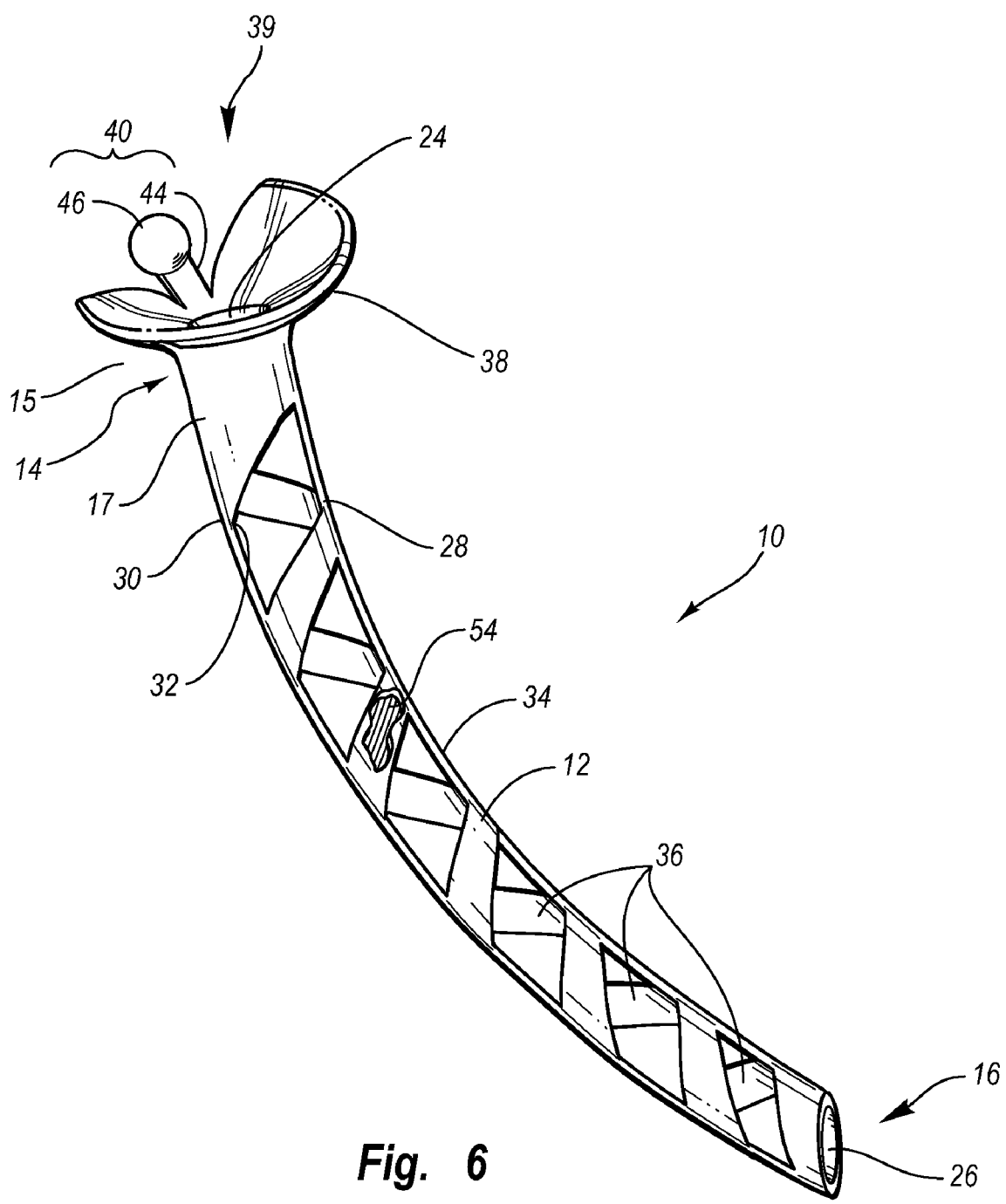

Apertures 36 allow air passing through air passage 22 to contact the lining of the nasal passageway. In turn the air helps to humidify the lining, thereby minimizing drying, irritation and cracking. In addition, by increasing the number of apertures 36 along device 10, the chance that air passage 22 will be constricted or occluded by bodily fluids decreases. For example, in one embodiment, such as depicted in FIG. 6, the number and placement of apertures 36 can be maximized so as to maximize the free flow of air through and around device 10. However, a sufficient portion of the structure of tubular body 12 is retained to prevent collapse of tubular body 12. In one embodiment, at least ⅓ of the surface area of the exterior surface of tubular body 12 comprises apertures 36. Alternatively, at least ½ of the surface area of the exterior surface of tubular body 12 comprises apertures 36. Other proportions can also be used. It is likewise appreciated that tubular body 12 can be formed without any apertures extending through sidewall 17. In this embodiment, air passage 22 only communicates with openings 24 and 26.

Returning to FIG. 1, a securement assembly 37 is disposed at the proximal end 14 of tubular body 12. In one exemplary embodiment, securement assembly 37 includes a flared flange 38 and a flexible locking protrusion 40 separated from the flared flange 38 by spaces 42. Flared flange 38 has a distal end 15 connected to tubular body 12 and an opposing proximal end 39. Proximal end 39 terminates at a perimeter edge 41. Flange 38 outwardly projects generally from front side 28, left side 32, and right side 34 of tubular body 12 while protrusion 40 generally projects from back side 30 of tubular body 12. In the embodiment depicted, flange 38 outwardly slopes from tubular body 12. In alternative embodiments, flange 38 can outwardly project normal to tubular body 12.

At at least perimeter edge 41, flange 38 has a size that is larger than the nostril opening leading to the nasal passageway for which the nasopharyngeal airway device 10 is intended to be used. Expressed in other terms, flange 38 is sufficiently sized and/or shaped so as to prevent flange 38 from freely passing into nasal passageway. As a result, flange 38 prevents device 10 from sliding back too far into the nasal passageway where it may become lodged or difficult to remove.

In one embodiment, perimeter edge 41 of flange 38 is slightly curved inward toward proximal end 39 so that the rounded edges prevent any trauma to the soft tissue. The diameter at perimeter edge 41 of flared flange 38 is typically in a range from about 2 cm to about 5 cm, although this may differ depending on the intended use of device 10. At distal end 15 of flared flange 38, the inner diameter can correspond to the inner diameter of passageway 22 of tubular body 12. The wall of flared flange 38 can have the same thickness as sidewall 17 of tubular body 12. Alternatively, the wall of flange 38 can be tapered or otherwise vary in shape and can have a different thickness than tubular body 12.

Flange 38 is also typically made of a soft, flexible material such as that discussed above with regard to tubular body 12. Flange 38 can be integrally molded with tubular body 12 or can be connected thereto such as by welding, adhesive, mechanical fastener, or the like.

As will be discussed below in greater detail, flange 38 can come in a variety of different configurations. For example, flange 38 can be designed to encircle a portion of tubular body 12 as show in FIGS. 1 and 2 or can encircle all of tubular body 12 so as to have a flat disk or frustoconical shape. In yet other embodiments, flange 38 can comprises a plurality of spaced apart flanges.

Figure 2:
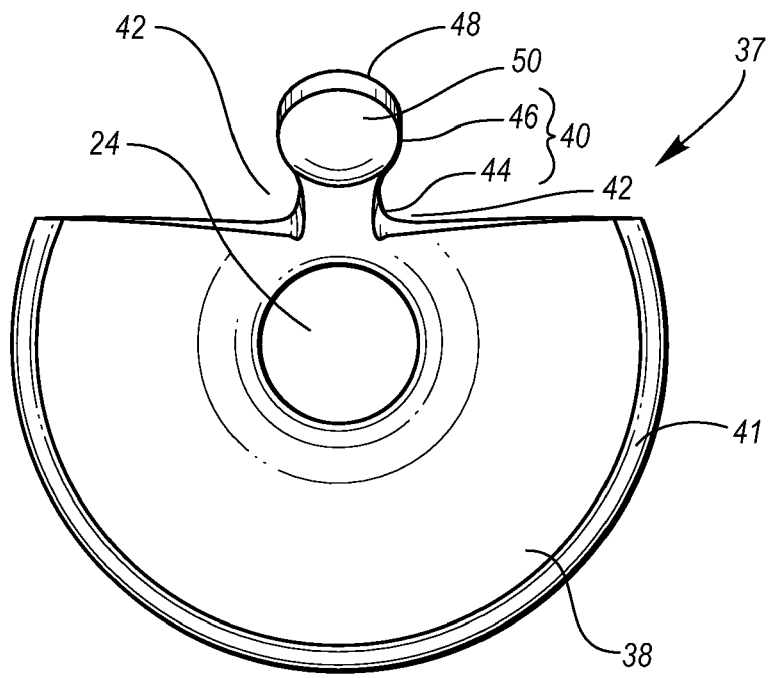
FIG. 2 is a top view of the embodiment of FIG. 1.

As also shown in FIGS. 1 and 2, locking protrusion 40 includes a stem 44 extending outwardly from proximal end 14 of tubular body 12 and terminating at a tip 46. Stem 44 can be integrally formed with or discretely connected to flared flange 38 or tubular body 12. In either case, stem 44 projects outwardly from proximal end 14 of tubular body 12 so that it functions to secure device 10 within the nasal passageway.

Figure 4:
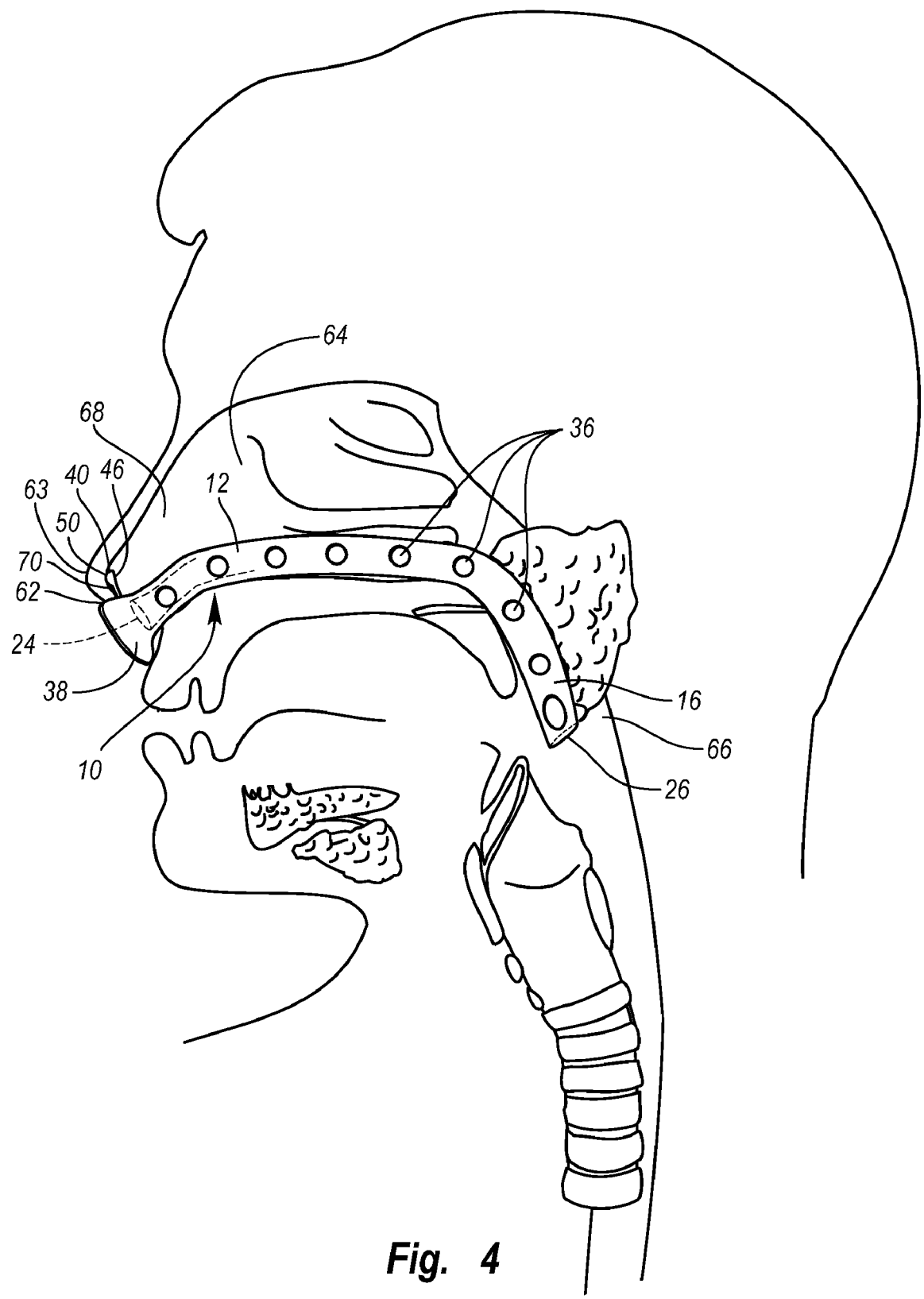
FIG. 4 a schematic view of the nasopharyngeal airway device of FIG. 1 inserted into a nasal passageway of a patient.

Specifically, during use, as depicted in FIG. 4, distal end 16 of tubular body 12 is advanced through a nostril opening 62 of a nose 63 and through a nasal passageway 64 until distal end 16 reaches an oropharynx 66. Nasal passageway 64 is bounded by lining 68. In this position, flange 38 is disposed adjacent to or against nostril opening 62. Again, flange 38 is larger than nostril opening 62 so that flange 38 cannot unintentionally slide into nasal passageway 64. In this position, opening 24 of nasopharyngeal airway device 10 communicates with the atmosphere while opening 26 communicates with oropharynx 66. As previously discussed, distal end 16 of tubular body 12 can be tapered at an angle so as to minimize trauma to lining 68 of nasal passageway 64 during insertion of device 10. In another embodiment, not shown, distal end 16 is rounded so as to minimize trauma during insertion of device 10. In one embodiment, a water based lubricant, such as Xylocaine® can be placed on distal end 16 of tubular body 12 to lubricate and/or anesthetize lining 68 of nasal passageway 64.

Once device 10 is disposed within nasal passageway 64, stem 44 of locking protrusion 40 is bent back toward distal end 16 and tip 46 is inserted within nostril opening 62 of nasal passageway 64. Locking protrusion 40 resiliently biases against lining 68 of nasal passageway 64 so as to secure device 10 within nasal passageway 64. Specifically, a recessed pocket 70 is formed within nasal passageway 64 at the tip of nose 63. Locking protrusion 40 is typically positioned on nasopharyngeal airway device 10 so as to catch within pocket 70. Opposing restraints are then used to secure device 10 in place. That is, flange 30 biases against the exterior surface of nose 63 or the lining of nasal opening 61 so as to prevent device 10 from further sliding into nasal passageway 64 while locking protrusion 40 biases against the lining of pocket 70 so as to prevent device 10 from unintentionally sliding out of nasal passageway 64. Accordingly, in the embodiment depicted in FIG. 4, locking protrusion 40 is configured such that at least the tip of locking provision 40 is disposed within the same nostril of the nasal passageway 64 as the nostril in which tubular body 12 is disposed when tubular body 12 is disposed within nasal passageway 64 and at least a portion of flange 30 is disposed outside of nasal passageway 64.

Locking protrusion 40 is typically formed from a flexible or semi-flexible material so that stem 44 can be bent backwards so as to place tip 46 in contact with lining 68 of nasal passageway 64. At the same time, locking protrusion 40 is sufficiently resilient to securely maintain device 10 within nasal passageway 64. In contrast to being resiliently flexible, locking protrusion 40 can be rigidly flexible. In this embodiment, once tip 46 is positioned within nasal passageway 64, locking protrusion 40 can be physically bent to catch against pocket 70.

In one embodiment, locking protrusion 40 can be constructed from the same types of materials as discussed above with regard to tubular body 12. However, for a discrete device 10, locking protrusion 40 can be made of the same material as tubular body 12 or a different material. It is also appreciated that locking protrusion 40 can be comprised of multiple materials. For example, locking protrusion 40 can comprise a base portion that is integrally formed with and made of the same material as tubular body 12. Locking protrusion 40 can further comprises a coating over the base portion made of a softer material such as a polymeric foam.

Locking protrusion 40 can be integrally formed with tubular body 12 and/or flange 38 such as by molding or other manufacturing processes. Alternatively, locking protrusion can be connected to flange 38 and/or tubular body 12 by co-molding, adhesive, welding, mechanical attachment or other means for securing.

FIGS. 2 and 3 further illustrate that tip 46 can have a relatively flat back side 48 and a rounded contact side 50. As contact side 50 is configured to contact lining 68 of nasal passageway 64, rounding of contact side 50 helps to minimize an trauma. Since the back side 48 of tip 46 generally does not contact lining 68, it is not necessary for back side 48 to be rounded, although in some embodiments it can be. In yet another embodiment, shown more clearly in FIG. 6, tip 46 can form a rounded ball.

In one embodiment, stem 44 can be integrally formed with tip 46. In another embodiment, tip 46 can be formed from a different or softer material than stem 44. For example, tip 46 could comprise a foam, rubber, or plastic or other polymeric material which is adhered to the stem 44 such as by adhesive, welding, coating, or other bonding techniques.

In typical embodiments, locking protrusion 40 has a length in a range from about 0.5 cm to about 2 cm. However, depending on the size of the patient, the size of locking protrusion 40 may vary. Ideally, the length of locking protrusion 40 is of sufficient length so that locking protrusion 40 can be easily and comfortably positioned within nasal passageway 64 and securely bias against lining 68.

As mentioned above, different materials can be used to form different elements of device 10. For example, securement assembly 37 may be formed from a slightly harder plastic than tubular body 12. Likewise, locking protrusion 40 may need to be a somewhat stiffer material than the rest of device 10 in order to securely fix device 10.

In contrast to varying stiffness by using different materials, stiffness or flexibility can also be varied by using reinforcing members. Turning back to FIG. 3, a reinforcing member 54 is embedded within and longitudinally extends along tubular body 12 and locking protrusion 40. Reinforcing member provides increased rigidity to locking protrusion 40. In contrast to being embedded, it is appreciated that reinforcing member can be placed along interior surface 20 or exterior surface 18. In one embodiment, reinforcing member 54 is in the form of an elongate rib. In other embodiments, reinforcing member 54 can comprise one or more filaments, strands, cords, lines, or the like.

It will be appreciated that reinforcing material can also be disposed on one or more of front side 28, back side 30, left side 32 and/or right side 34 and can be disposed linearly, transversely, or spirally along nasopharyngeal airway device 10 or parts thereof For example, depicted in FIG. 6 reinforcing member 54 is spirally embedded within tubular body 12 so as to reinforce tubular body 12, thereby enabling easy insertion and preventing collapse. The reinforcement members 54 can comprised of plastic, rubber or other polymeric materials having different stiffness, sizes, and forms. In one embodiment, reinforcement members 54 can be co-molded or co-extruded with nasopharyngeal airway device 10.

Figure 5:
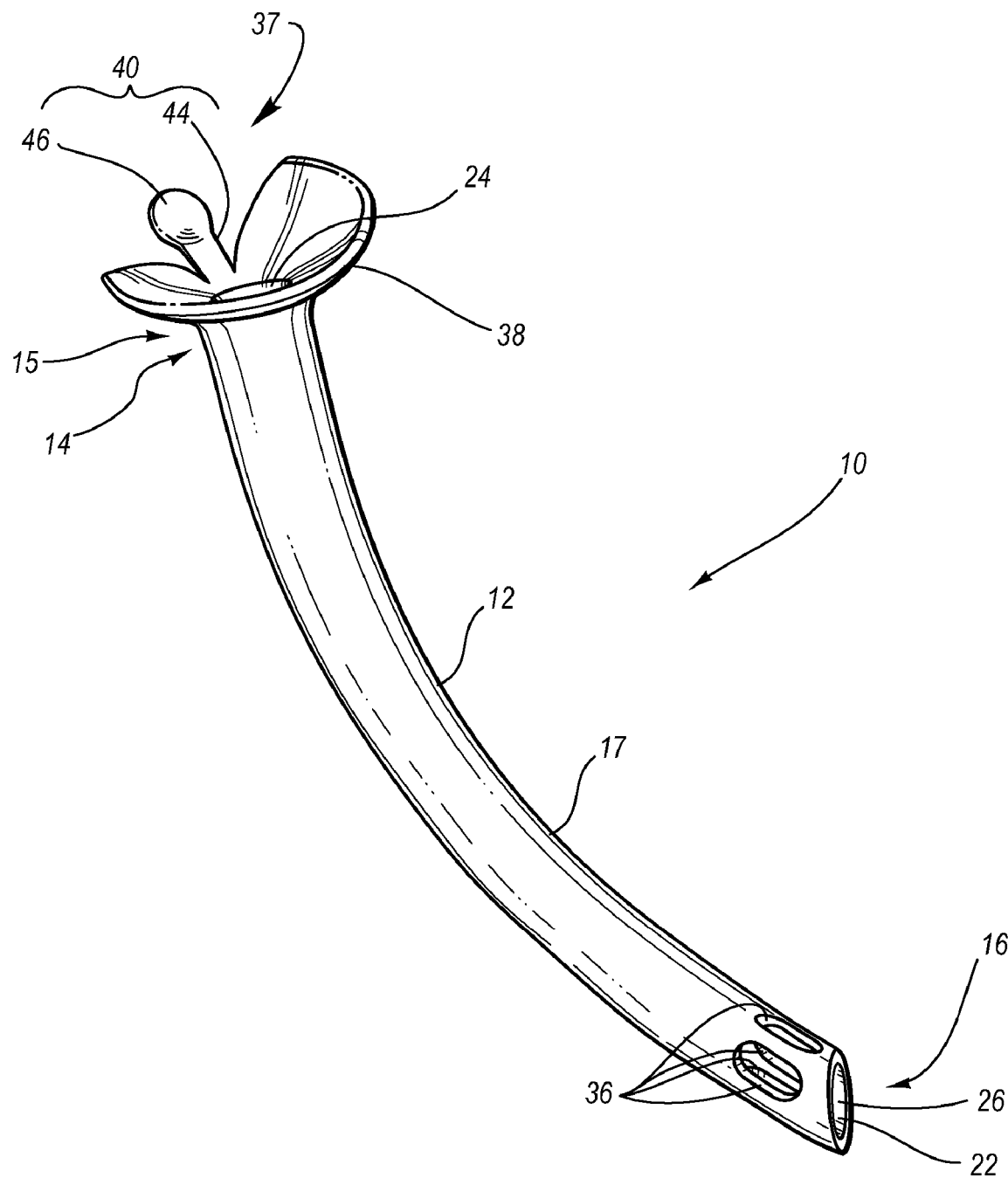
FIGS. 5 and 6 are perspective views of alternative embodiments of the nasopharyngeal airway device shown in FIG. 1.

With reference now to FIG. 5, another embodiment of apertures 36 is illustrated. As shown in FIG. 5, a plurality of apertures 36, such as two, three, or more, are formed at the distal end 16 of tubular body 12. Apertures 36 radially encircle tubular body 12 and communicate with air passage 22. Apertures 36 perform substantially the same function as described above. That is, apertures 36 assist in humidifying the nasal passageway 64 to provide comfort to the patient and help prevent obstruction of air passage 22.

FIG. 6 illustrates yet another embodiment of device 10. FIG. 6 illustrates tip 46 of locking protrusion 40 being formed as a rounded ball. In addition, in FIG. 6 apertures 36 have been maximized along the length of tubular body 12 so as to maximize air flow to lining 68 along nasal passageway 64 (FIG. 4). In this embodiment, apertures 36 are formed as diagonal slots along tubular body 12. In one embodiment, one row of slots is formed on left side 32 of tubular body 12 while an opposing row of slots is formed on right side 34 of tubular body 12. These slots on left side 32 and right side 34 can be configured so that they do not align with each other. In addition, the configuration of apertures 36 may assist to increase the bendability or flexibility of tubular body 12.

In embodiments where apertures 36 may be larger, such as that shown in FIG. 6, reinforcement member 54, as discussed above, can be placed in sidewall 17 of tubular body 12 between apertures 36 to strengthen tubular body 12. Reinforcing members 54 increase the strength of tubular body 12 so as to prevent unwanted collapse or kinking during insertion and use. In addition, reinforcement material 54, for example in the form of reinforcement ribs, may still be disposed on front side 28 or back side 30 of tubular body 12.

In one embodiment of the present invention, means are provided for limiting advancement of tubular body 12 into a nasal passageway. Means are also provided for securing tubular body 12 within the nasal passageway. One example of the means for limiting is flange 38 and the alternatives thereto as discussed above. One example of the means for securing is locking protrusion 40 and the alternatives thereto as discussed above. Depicted in FIGS. 7-13 are still other embodiments of means for limiting and means for securing.

Figure 7:
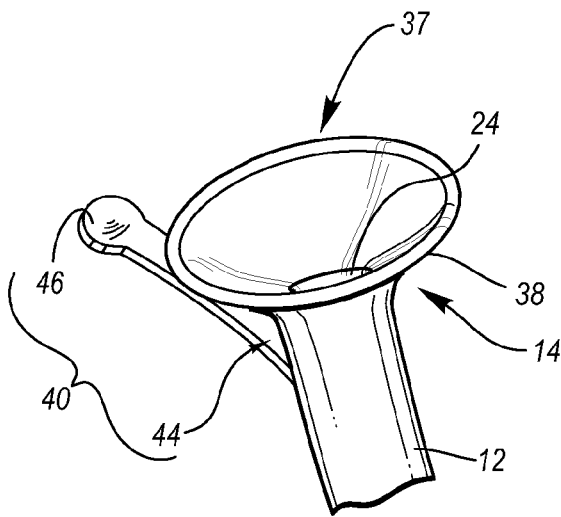
FIGS. 7-13 are perspective views of alternative embodiments of the securement assembly of the nasopharyngeal airway device shown in FIG. 1.

As shown in FIG. 7, flared flange 38 completely encircles tubular body 12 so as to have a substantially frustoconical configuration. Furthermore, FIG. 7 illustrates locking protrusion 40 connected to and extending from tubular body 12. Locking protrusion 40 is still configured to be bent backward into the nasal passageway to secure device 10 thereto. Locking protrusion 40 and flared flange 38 continue to cooperate to form securement assembly 37.

Figure 8:
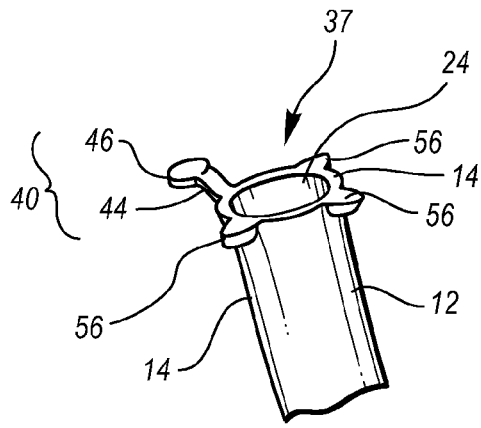

Depicted in FIG. 8, flared flange 38 has been replaced by a plurality of spaced apart flanges 56 that radially outwardly project from proximal end 14 of tubular body 12. Flanges 56 are sized so that proximal end 14 of tubular body 12 cannot freely pass through nostril opening 62. As such, flanges 56 still function to limit advancement of tubular body 12 into nasal passageway 64. Locking protrusion 40 is also shown projecting directly from proximal end 14 of tubular body 12.

Figure 9:
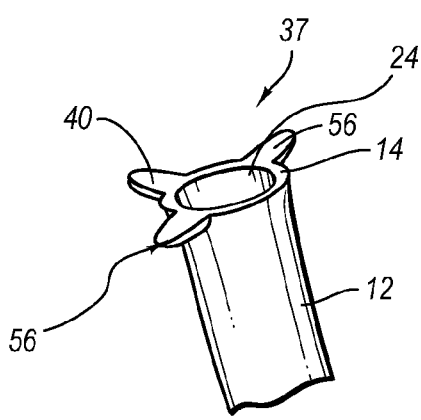

Turning to FIG. 9, it is appreciated that locking protrusion 40 can have substantially the same configuration as flanges 56. That is, locking protrusion 40 need not have an enlarged rounded head formed on the end thereof.

Figure 10:
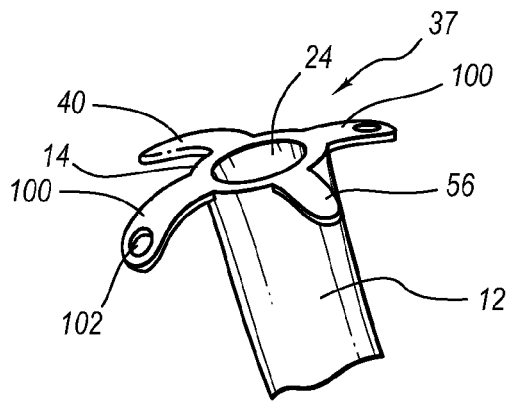
Figure 11:
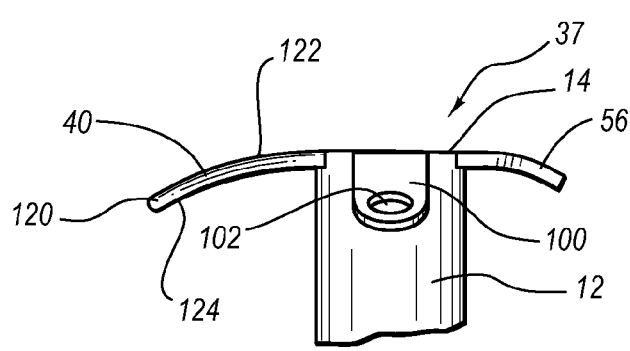

Depicted in FIGS. 10 and 11, locking protrusion 40 extends out from proximal end 14 of tubular body 12 and curves back toward distal end 16. In this configuration, locking protrusion 40 more closely follows the contour of nasal passageway 64 when locking protrusion 40 is inserted inside nasal passageway 64. As a result, locking protrusion 40 biases against lining 68 using more surface area of locking protrusion 40. A larger biasing area results in a stronger securement. The contour matching also provides greater comfort for the patient.

In the embodiment depicted locking protrusion 120 has a perimeter edge 120 that extends between a top surface 122 and an opposing bottom surface 124. Although not required, to provide greater comfort for the patient, it is desirable that perimeter edge 120 be rounded so that edge 120 has less likelihood of catching on and/or damaging nasal tissue. As discussed above, locking protrusion 40, and particularly the terminal end thereof, can have a variety of different configurations. For example, the terminal end of locking protrusion can radially outwardly extend in the plane of locking protrusion and/or further rounded protrusions can be formed on one or both of top surface 122 and bottom surface 124. A rounded loop of increased thickness can be formed at the terminal end and/or a hole, such as hole 102 discussed below, can be formed through the terminal end of locking protrusion 40. In other embodiments it is appreciated that locking protrusion can have a circular, elliptical, or other rounded transverse cross section along the length thereof. Any other shape that will help retain locking protrusion 40 within the nasal passageway without damaging nasal tissue can also be used.

Furthermore, FIGS. 10 and 11 illustrate lateral flanges 100 which are curved back toward distal end 16. As opposed to many of the flanges 56 discussed above, lateral flanges 100 would need to bend back against their natural curvature to allow proximal end 14 of tubular body 12 to pass into nostril opening 62. This would require more force to do so. As a result, the reversed curvature provides a greater limiting force to help prevent proximal end 14 of tubular body 12 from passing through nostril opening 62.

As a result of the backwards curvature, when the tubular body 12 has been inserted into one of the nostrils, one of the lateral flanges 100 will likely be positioned at least partially within the nostril opening of the other nostril. To compensate for this, an hole 102 is formed in each lateral flange 100 to allow air to flow more freely within the other nostril. The hole extends between the top surface and opposing bottom surface of the flange. If a nasogastric (NG) tube is used in the other nostril, the NG tube can be inserted through hole 102, if desired by the medical personnel.

Figure 12:
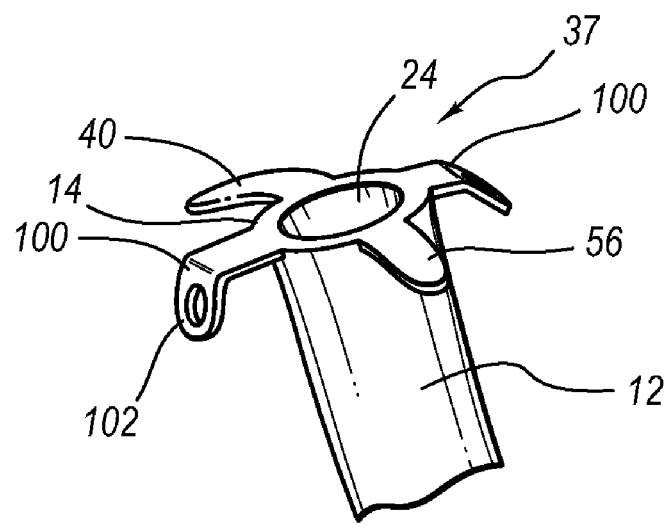

In an alternative embodiment shown in FIG. 12, the lateral flanges 100 first extend orthogonally out from proximal end 14 of tubular body 12, and then angle down back the distal end 16 at a defined angle. As in the previous embodiment, this provides a greater limiting force to help prevent proximal end 14 of tubular body 12 from passing through nostril opening 62.

Figure 13:
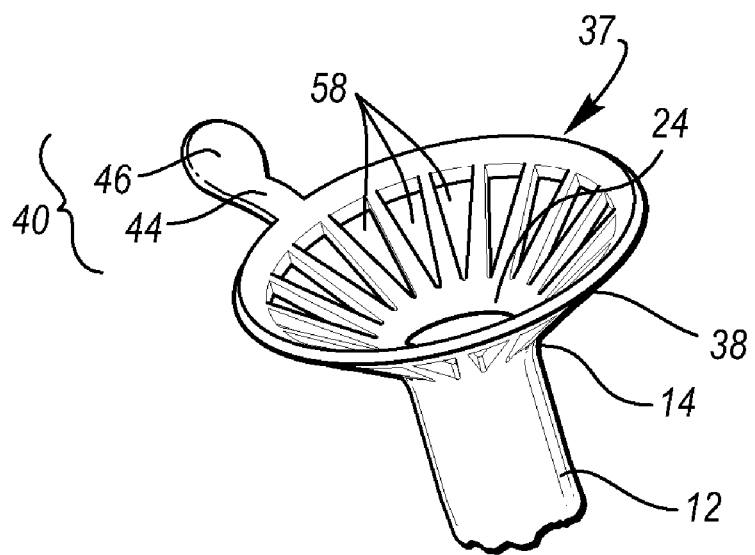

Finally, as shown in FIG. 13, flared flange 38 may include a plurality of apertures 58 extending therethrough. Locking protrusion 40 can also extend from flared flange 38 and perform the same function as discussed above. Flared flange 38 and protrusion 40 continue to cooperate to form securement assembly 37. Other types of means for limiting and means for securing can also be used.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method comprising:
   advancing a distal end of a tubular nasopharyngeal airway device through a nostril opening and into a nasal passageway of a patient, the nasopharyngeal airway device having a proximal end that is larger than the nostril opening;
   manually bending a resiliently flexible elongated locking protrusion that projects from the proximal end of the nasopharyngeal airway device back toward the distal end of the nasopharyngeal airway device; and
   inserting at least a terminal tip of the locking protrusion into the same nostril opening in which the nasopharyngeal airway device is disposed so that the locking protrusion biases against the lining of the nasal passageway, thereby securing the nasopharyngeal airway device within the nasal passageway.

2. The method as recited in claim 1, wherein the act of advancing comprises advancing the distal end of the tubular nasopharyngeal airway device through the nostril opening and into the nasal passageway of the patient, the tubular nasopharyngeal airway device having at least one flange outwardly projecting from the proximal end thereof to limit advancement of the proximal end into the nostril opening.

3. The method as recited in claim 1, wherein the act of advancing comprises advancing the distal end of the tubular nasopharyngeal airway device through the nostril opening and into the nasal passageway of a patient, the tubular nasopharyngeal airway device having a plurality of flanges outwardly projecting from the proximal end thereof to limit advancement of the proximal end into the nostril opening.

4. The method as recited in claim 1, wherein the act of inserting comprises inserting a rounded ball disposed at the terminal tip of the resiliently flexible elongated locking protrusion into the same nostril opening as the nostril opening in which the nasopharyngeal airway device is disposed.

5. The method as recited in claim 1, wherein the tip of the elongated locking protrusion comprises a rounded ball.

6. The method as recited in claim 1, wherein the tubular nasopharyngeal airway device comprises a tubular body having at least one flange outwardly projecting from the proximal end thereof.

7. The method as recited in claim 6, wherein the tubular nasopharyngeal airway device further comprises a reinforcing member embedded within and extending between the tubular body and the elongated locking protrusion.

8. The method as recited in claim 6, wherein a plurality of spaced apart openings extend through the tubular body so as to communicate with the nasal passageway.

9. The method as recited in claim 8, wherein the openings radially encircle or extend along the length of the tubular body.

10. A method comprising:

advancing a distal end of a tubular nasopharyngeal airway device through a nostril opening and into a nasal passageway of a patient, the nasopharyngeal airway device having means for limiting advancement of a proximal end of the nasopharyngeal airway device into the nostril opening; and bending a resiliently flexible elongated locking protrusion projecting from the proximal end of the nasopharyngeal airway device back toward the distal end of the nasopharyngeal airway device after the step of advancing; and inserting a terminal tip of the bent resiliently flexible elongated locking protrusion into the same nostril opening as the nostril opening in which the nasopharyngeal airway device is disposed so that the locking protrusion biases against the lining of the nasal passageway, thereby securing the nasopharyngeal airway device within the nasal passageway.

11. The method as recited in claim 10, further comprising manually bending the locking protrusion back towards the distal end of the nasopharyngeal airway device before performing the act of inserting.

12. The method as recited in claim 10, wherein the means for limiting advancement comprises one or more flanges outwardly projecting from the proximal end of the nasopharyngeal airway device.

13. A method comprising:

advancing a distal end of a tubular nasopharyngeal airway device through a nostril opening and into a nasal passageway of a patient, the nasopharyngeal airway device having a proximal end with one or more flanges outwardly projecting therefrom;

manually bending a resiliently flexible elongated locking protrusion that projects from the proximal end of the nasopharyngeal airway device back toward the distal end of the nasopharyngeal airway device; and inserting at least a terminal tip of the locking protrusion into the same nostril opening in which the nasopharyngeal airway device is disposed so that the locking protrusion biases against the lining of the nasal passageway, thereby securing the nasopharyngeal airway device within the nasal passageway.

14. The method as recited in claim 10, wherein the terminal tip biases against the lining of the nasal passageway.

15. The method as recited in claim 10, wherein only a single locking protrusion biases against the lining of the nasal passageway.

\* \* \* \* \*

UNITED STATES PATENT AND TRADEMARK OFFICE
CERTIFICATE OF CORRECTION

PATENT NO. : 7,730,888 B2  Page 1 of 2
APPLICATION NO. : 11/468158
DATED : June 8, 2010
INVENTOR(S) : Dunlap It is certified that error appears in the above-identified patent and that said Letters Patent is hereby corrected as shown below:

Drawings
Sheet 1, replace Figure 1 with the figure depicted below, wherein the second instance of "16" is removed.

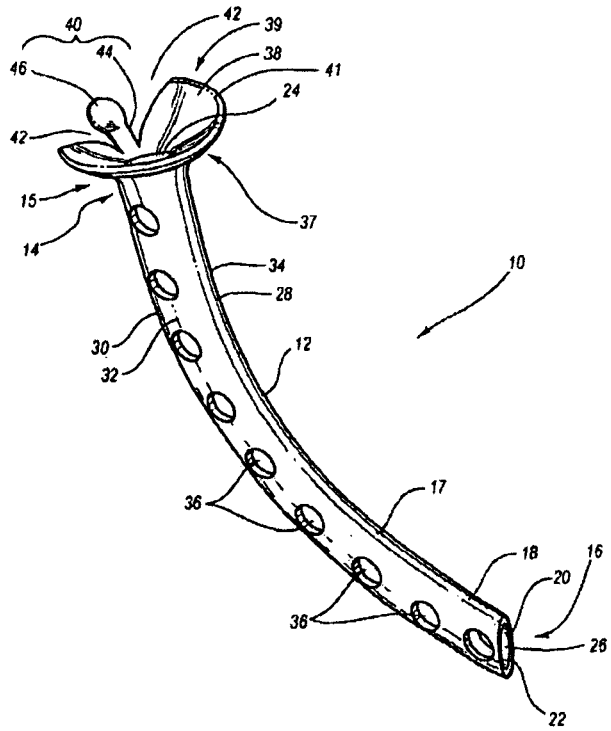

Fig. 1

Signed and Sealed this
Fourth Day of January, 2011

David J. Kappos
*Director of the United States Patent and Trademark Office*

CERTIFICATE OF CORRECTION (continued)

U.S. Pat. No. 7,730,888 B2

Column 1 Line 23, change "devices is" to --device is--
Line 26, change "breath" to --breathe--
Line 57, change "patent" to --patient--

Column 2 Line 62, change "thereof This" to --thereof. This--

Column 4 Line 26, change "can comprises" to --can comprise--
Line 64, change "30" to --38--
Line 65, change "nasal opening 61" to --nostril opening 62--

Column 5
Line 4, change "provision 40" to --protrusion 40--
Line 8, change "flange 30" to --flange 38--
Line 29, change "comprises" to --comprise--
Line 33, change "locking protrusion" to --locking protrusion 40--
Line 41, change "an trauma" to --a trauma--

Column 6
Line 5, change "member" to --member 54--
Line 14, change "thereof For" to --thereof. For--
Line 18, change "can comprised" to --can be comprised--
Line 45, change "reinforcement member 54" to --reinforcing member 54--
Line 50, change "reinforcement material 54" to --reinforcing member 54--
Line 66, change "backward" to --backwards--

Column 7 Line 25, change "depicted locking protrusion 120" to --depicted, locking protrusion 40--
Line 33, change "locking protrusion" to --locking protrusion 40--
Line 40, change "locking protrusion" to --locking protrusion 40--
Line 59, change "hole" to --hole 102--

Column 8 Line 2, change "nostril opening" to --nasal opening--